US 8,764,774 B2
Jul. 1, 2014

(12) United States Patent
Sigmon, Jr.

(10) Patent No.: US 8,764,774 B2
(45) Date of Patent: Jul. 1, 2014

(54) CLIP SYSTEM HAVING TETHER SEGMENTS FOR CLOSURE

(75) Inventor: John C. Sigmon, Jr., Greensboro, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/290,580

(22) Filed: Nov. 7, 2011

(65) Prior Publication Data

US 2012/0116419 A1    May 10, 2012

Related U.S. Application Data

(60) Provisional application No. 61/411,709, filed on Nov. 9, 2010.

(51) Int. Cl.
*A61B 17/08* (2006.01)

(52) U.S. Cl.
USPC ............. 606/151; 606/139; 606/142; 24/535

(58) Field of Classification Search
USPC ........... 606/75, 120, 135, 139, 142, 143, 151, 606/157, 158, 213, 219, 220, 221; 227/175.1–182.1, 901, 902; 24/535
See application file for complete search history.

(56) References Cited

U.S. PATENT DOCUMENTS

| 943,263 | A | | 12/1909 | Moraweck |
|---|---|---|---|---|
| 1,031,306 | A | * | 7/1912 | Williams ........................ 24/535 |
| 1,510,416 | A | | 9/1924 | Pietz et al. |
| 1,578,800 | A | | 3/1926 | Brandenberger |
| 2,113,246 | A | | 4/1938 | Wappler |
| 2,384,697 | A | | 9/1945 | Riccardi |
| 2,968,041 | A | | 1/1961 | Skold |
| 3,378,010 | A | | 4/1968 | Codling et al. |
| 3,518,993 | A | | 7/1970 | Blake |
| 3,616,497 | A | | 11/1971 | Esposito, Jr. |
| 3,777,538 | A | | 12/1973 | Weatherly et al. |

(Continued)

FOREIGN PATENT DOCUMENTS

| DE | 19534320 | 2/1997 |
|---|---|---|
| DE | 298 11 510 | 6/1998 |

(Continued)

OTHER PUBLICATIONS http://www.thefreedictionary.com/flare, dictionary definition of the term "flared" retrieved Jul. 28, 2013.*

(Continued)

*Primary Examiner* — David Eastwood
(74) *Attorney, Agent, or Firm* — Brinks Gilson & Lione (57) ABSTRACT

The present embodiments provide systems and methods for deploying at least one clip during a medical procedure. In one embodiment, the system comprises a clip having first and second arms. A locking pin is coupled to the clip and disposed for incremental movement relative to the clip. Further, a tether is coupled to the locking pin, wherein a first tether segment is secured to a distal region of the second arm, and a second tether segment is secured to a distal region of the first arm. In use, proximal retraction of the locking pin causes a proximal retraction of the first and second tether segments to move the clip between open and closed states. Incremental retraction of the locking pin incrementally advances the clip between the open and closed states.

12 Claims, 6 Drawing Sheets

(56) References Cited

U.S. PATENT DOCUMENTS

| | | | | |
|---|---|---|---|---|
| 3,882,854 | A | 5/1975 | Hulka et al. | |
| 3,958,576 | A | 5/1976 | Komiya | |
| 4,038,987 | A | 8/1977 | Komiya | |
| 4,046,149 | A | 9/1977 | Komiya | |
| 4,169,476 | A | 10/1979 | Hiltebrandt | |
| 4,215,871 | A | 8/1980 | Hirsch et al. | |
| 4,367,746 | A | 1/1983 | Derechinsky | |
| 4,394,861 | A | 7/1983 | Sciortino | |
| 4,394,864 | A | 7/1983 | Sandhaus | |
| 4,446,865 | A | 5/1984 | Jewusiak | |
| 4,458,682 | A | 7/1984 | Cerwin | |
| 4,485,817 | A | 12/1984 | Swiggett | |
| 4,496,090 | A | 1/1985 | Crevier et al. | |
| 4,512,345 | A | 4/1985 | Green | |
| 4,681,107 | A | 7/1987 | Kees, Jr. | |
| 4,706,668 | A | 11/1987 | Backer | |
| 4,714,075 | A | 12/1987 | Krauter et al. | |
| 4,735,194 | A | 4/1988 | Stiegmann | |
| 4,759,364 | A | 7/1988 | Boebel | |
| 4,796,627 | A | 1/1989 | Tucker | |
| 4,821,721 | A | 4/1989 | Chin et al. | |
| 4,835,824 | A | 6/1989 | Durham et al. | |
| 4,841,888 | A | 6/1989 | Mills et al. | |
| 4,880,015 | A | 11/1989 | Nierman | |
| 4,887,612 | A | 12/1989 | Esser et al. | |
| 4,934,364 | A | 6/1990 | Green | |
| 4,945,920 | A | 8/1990 | Clossick | |
| 4,971,067 | A | 11/1990 | Bolduc et al. | |
| 4,983,176 | A | 1/1991 | Cushman et al. | |
| 5,015,249 | A | 5/1991 | Nakao et al. | |
| 5,049,153 | A | 9/1991 | Nakao et al. | |
| 5,062,848 | A | 11/1991 | Frazee et al. | |
| 5,100,418 | A | 3/1992 | Yoon et al. | |
| 5,112,343 | A | 5/1992 | Thornton | |
| 5,156,609 | A | 10/1992 | Nakao et al. | |
| 5,222,961 | A | 6/1993 | Nakao et al. | |
| 5,242,456 | A | 9/1993 | Nash et al. | |
| 5,300,081 | A | 4/1994 | Young et al. | |
| 5,304,183 | A | 4/1994 | Gourlay et al. | |
| 5,366,459 | A | 11/1994 | Yoon | |
| 5,395,381 | A | 3/1995 | Green et al. | |
| 5,441,509 | A | 8/1995 | Vidal et al. | |
| 5,445,167 | A | 8/1995 | Yoon et al. | |
| 5,464,416 | A | 11/1995 | Steckel | |
| 5,474,567 | A | 12/1995 | Stefanchik et al. | |
| 5,486,185 | A | 1/1996 | Freitas et al. | |
| 5,514,148 | A | 5/1996 | Smith, III | |
| 5,520,701 | A | 5/1996 | Lerch | |
| 5,527,319 | A | 6/1996 | Green et al. | |
| 5,540,124 | A | 7/1996 | Srhoj | |
| 5,545,180 | A * | 8/1996 | Le et al. | 606/232 |
| 5,569,274 | A | 10/1996 | Rapacki et al. | |
| 5,601,574 | A | 2/1997 | Stefanchik et al. | |
| 5,634,932 | A | 6/1997 | Schmidt | |
| 5,695,504 | A | 12/1997 | Gifford, III et al. | |
| 5,700,271 | A | 12/1997 | Whitfield et al. | |
| 5,702,411 | A | 12/1997 | Back et al. | |
| 5,733,329 | A | 3/1998 | Wallace et al. | |
| 5,766,184 | A | 6/1998 | Matsuno et al. | |
| 5,766,189 | A | 6/1998 | Matsuno | |
| 5,782,747 | A | 7/1998 | Zimmon | |
| 5,895,394 | A | 4/1999 | Kienzle et al. | |
| 5,980,534 | A | 11/1999 | Gimpelson | |
| 5,989,268 | A | 11/1999 | Pugsley, Jr. et al. | |
| 6,001,110 | A | 12/1999 | Adams | |
| RE36,720 | E | 5/2000 | Green et al. | |
| 6,139,555 | A | 10/2000 | Hart et al. | |
| 6,155,968 | A | 12/2000 | Wilk | |
| 6,167,605 | B1 | 1/2001 | Morales | |
| 6,193,733 | B1 | 2/2001 | Adams | |
| 6,267,776 | B1 | 7/2001 | O'Connell | |
| 6,350,269 | B1 | 2/2002 | Shipp et al. | |
| 6,352,541 | B1 | 3/2002 | Kienzle et al. | |
| 6,464,710 | B1 | 10/2002 | Foster | |
| 6,814,742 | B2 | 11/2004 | Kimura et al. | |
| 6,991,634 | B2 | 1/2006 | Sugiyama et al. | |
| 7,094,245 | B2 * | 8/2006 | Adams et al. | 606/142 |
| 7,713,284 | B2 * | 5/2010 | Crofford | 606/219 |
| 7,879,052 | B2 * | 2/2011 | Adams et al. | 606/157 |
| 8,276,300 | B2 * | 10/2012 | Huang | 40/799 |
| 8,444,660 | B2 * | 5/2013 | Adams et al. | 606/157 |
| 2001/0049497 | A1 | 12/2001 | Kalloo et al. | |
| 2002/0032462 | A1 | 3/2002 | Houser et al. | |
| 2002/0045909 | A1 | 4/2002 | Kimura et al. | |
| 2002/0055750 | A1 | 5/2002 | Durgin et al. | |
| 2002/0062130 | A1 | 5/2002 | Jugenheime et al. | |
| 2002/0128667 | A1 | 9/2002 | Kobayashi et al. | |
| 2002/0133178 | A1 | 9/2002 | Muramatsu et al. | |
| 2002/0138083 | A1 | 9/2002 | Muramatsu et al. | |
| 2002/0138085 | A1 | 9/2002 | Muramatsu et al. | |
| 2002/0147463 | A1 * | 10/2002 | Martinek | 606/232 |
| 2002/0151916 | A1 | 10/2002 | Muramatsu et al. | |
| 2002/0173805 | A1 | 11/2002 | Matsuno et al. | |
| 2003/0069592 | A1 * | 4/2003 | Adams et al. | 606/142 |
| 2003/0069593 | A1 | 4/2003 | Tremulis et al. | |
| 2003/0120341 | A1 * | 6/2003 | Shennib et al. | 623/2.12 |
| 2004/0092978 | A1 | 5/2004 | Surti | |
| 2005/0033312 | A1 | 2/2005 | Suzuki | |
| 2005/0055039 | A1 | 3/2005 | Burnett et al. | |
| 2005/0119698 | A1 * | 6/2005 | Martinek | 606/232 |
| 2005/0143767 | A1 | 6/2005 | Kimura | |
| 2005/0182426 | A1 * | 8/2005 | Adams et al. | 606/142 |
| 2005/0192599 | A1 | 9/2005 | Demarais | |
| 2008/0077144 | A1 * | 3/2008 | Crofford | 606/75 |

FOREIGN PATENT DOCUMENTS

| | | |
|---|---|---|
| DE | 100 11 292 | 8/2000 |
| DE | 101 16 168 A1 | 11/2001 |
| EP | 0 738 501 | 10/1996 |
| EP | 1493392 | 1/2005 |
| EP | 1604614 | 12/2005 |
| WO | WO 99/20183 | 4/1999 |
| WO | WO 00/21443 | 4/2000 |
| WO | WO 03/30746 | 4/2003 |

OTHER PUBLICATIONS

International Preliminary Report on Patentability for PCT/US2011/059564 issued May 14, 2013, 8 pgs.
Partial International Search Report for PCT/US07/12754 dated Dec. 11, 2007.
International Search Report for PCT Application No. PCT/US03/11496 dated Jul. 11, 2003.
International Search Report for PCT Application No. PCT/US03/11820 dated Jul. 11, 2003.
Office Action for Canadian Patent Application Serial No. 2,654,004 dated Oct. 15, 2009, 3 pgs.
Office Action for European Patent Application Serial No. 07 777 322.4 dated May 25, 2010, 3 pgs.
Office Action for Canadian Patent Application Serial No. 2,654,004 dated Jul. 28, 2010, 2 pgs.
International Search Report and Written Opinion for PCT/US2011/059564 mailed Feb. 9, 2012, 16 pgs.

* cited by examiner

CLIP SYSTEM HAVING TETHER SEGMENTS FOR CLOSURE

PRIORITY CLAIM

This invention claims the benefit of priority of U.S. Provisional Application Ser. No. 61/411,709, entitled "Clip System Having Tether Segments for Closure," filed Nov. 9, 2010, the disclosure of which is hereby incorporated by reference in its entirety.

BACKGROUND

Conventionally, a clip may be introduced into a body cavity through an endoscope to to grasp living tissue of a body cavity for hemostasis, marking, and/or ligating. In addition, clips are now being used in a number of applications related to gastrointestinal bleeding such as peptic ulcers, Mallory-Weiss tears, Dieulafoy's lesions, angiomas, post-papillotomy bleeding, and small varices with active bleeding.

Gastrointestinal bleeding is a somewhat common and serious condition that is often fatal if left untreated. This problem has prompted the development of a number of endoscopic therapeutic approaches to achieve hemostasis such as the injection of sclerosing agents and contact thermo-coagulation techniques. Although such approaches are often effective, bleeding continues for many patients and corrective surgery therefore becomes necessary. Because surgery is an invasive technique that is associated with a high morbidity rate and many other undesirable side effects, there exists a need for highly effective, less invasive procedures.

Mechanical hemostatic devices have been used in various parts of the body, including gastrointestinal applications. Such devices are typically in the form of clamps, clips, staples and tethers, which are able to apply sufficient constrictive forces to blood vessels so as to limit or interrupt blood flow. One of the problems associated with conventional hemostatic devices, however, is that many devices are not strong enough to cause permanent hemostasis.

Additionally, it may be difficult to progressively close a plurality of arms of a clip device. In particular, many clips comprise an open state where the plurality of arms are spaced apart from one another, wherein tissue may be positioned within the arms in the open state. Such clips further comprise closed states in which the arms are adjacent to one another, wherein the arms impose a compressive force upon the tissue in an effort to cause hemostasis. In some clips, a cannula is distally advanced over the arms to move the arms between the open and closed states. Generally, the clip is either in an open or closed state, but most clips cannot be incrementally closed, i.e., the first and second arms cannot be securely locked in any number of incremental positions.

SUMMARY

The present embodiments provide systems and methods for deploying at least one clip during a medical procedure. In one embodiment, the system comprises a clip having first and second arms, wherein distal regions of the first and second arms tend to be spaced apart from each other when the clip is in an open state, and wherein the distal regions of the first and second arms are adjacent to each other when the clip is in a closed state. A locking pin is coupled to the clip and disposed for incremental movement relative to the clip. Further, a tether is coupled to the locking pin, wherein a first tether segment is secured to the distal region of the second arm, and a second tether segment is secured to the distal region of the first arm. In use, proximal retraction of the locking pin causes a proximal retraction of the first and second tether segments to move the clip between the open and closed states.

In one embodiment, the tether is coupled to the locking pin through a bore formed in the locking pin. The first tether segment may be guided through a bore formed in the first arm at a location proximal to attachment of the first tether segment to the distal region of the second arm. The second tether segment may be guided through a bore formed in the second arm at a location proximal to attachment of the second tether segment to the distal region of the first arm. Additionally, a retainer is releasably coupled to the locking pin, such that proximal retraction of the retainer causes proximal retraction of the locking pin.

In one embodiment, the clip comprises a base region having a bore formed longitudinally therethrough, wherein proximal regions of the first and second arms extend distally away from the base region, and wherein at least a portion of the locking pin is disposed through the bore in the base region. The locking pin may comprise at least one region having a first diameter, and further may comprise at least one flared region having a second diameter, wherein the second diameter is greater than the first diameter. The second diameter of the flared region is greater than a diameter of the bore of the base region such a sufficient force must be imposed to incrementally proximally retract the locking pin through the base region of the clip.

Advantageously, incremental retraction of the locking pin facilitates incremental retraction of the first and second tether segments, which in turn incrementally advances the clip between open and closed states. In this manner, the clip may be incrementally closed and the first and second arms may be locked in any number of incremental positions.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Figure 1:
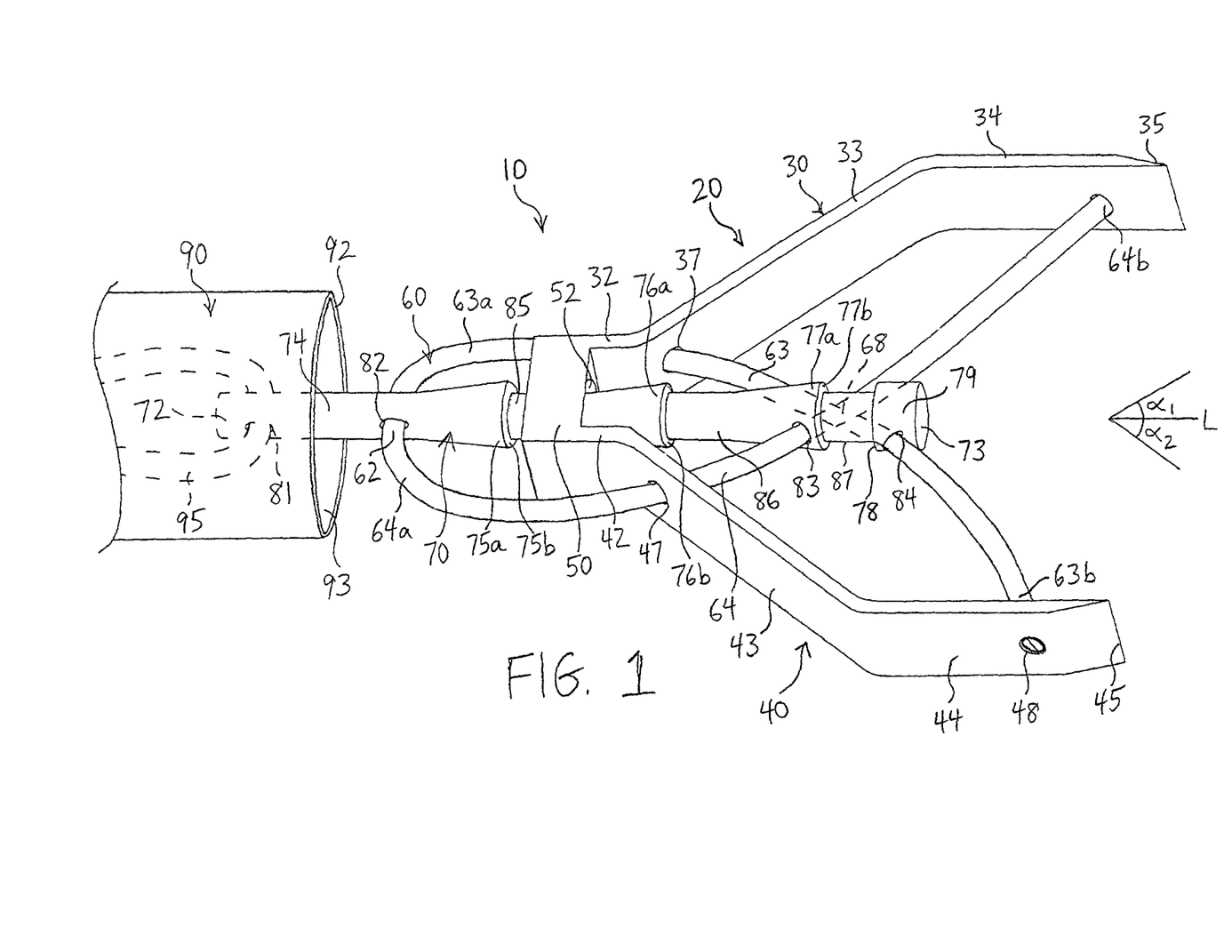
FIG. 1 is a perspective view showing components of a clip system with a clip in an open state.

Referring now to FIG. 1, a first embodiment of a clip system 10 is shown. In this embodiment, the clip system 10 comprises a clip 20, and further comprises a tether 60, a locking pin 70, and a delivery catheter 90, each of which are explained in detail below.

The clip 20 comprises a first arm 30 and a second arm 40. The first arm 30 has a proximal region 32, a distal region 34, and a tapered central region 33 extending therebetween, as shown in FIG. 1. Similarly, the second arm 40 has a proximal region 42, a distal region 44, and a tapered central region 43 extending therebetween.

Figure 2:
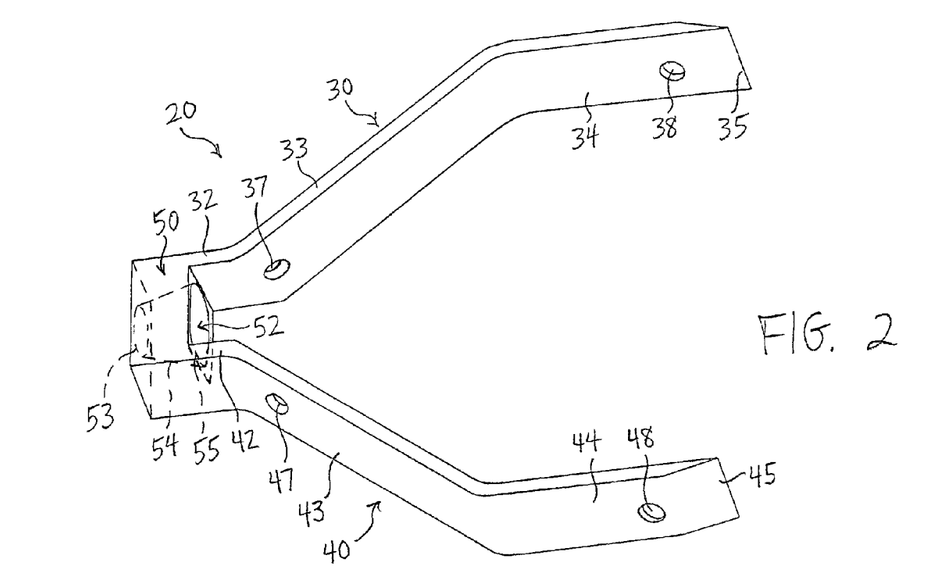
FIG. 2 is a perspective view showing the clip of FIG. 1 in isolation.

The proximal region 32 of the first arm 30 and the proximal region 42 of the second arm 40 are joined together at a base region 50 of the clip 20, as shown in FIGS. 1-2. The first and second arms 30 and 40 of the clip device 20 may be formed integrally with the base region 50, or alternatively, the first and second arms 30 and 40 may be secured to the base region 50 using an adhesive, solder, weld, mechanical attachment device, or any other suitable mechanism.

Figure 4:
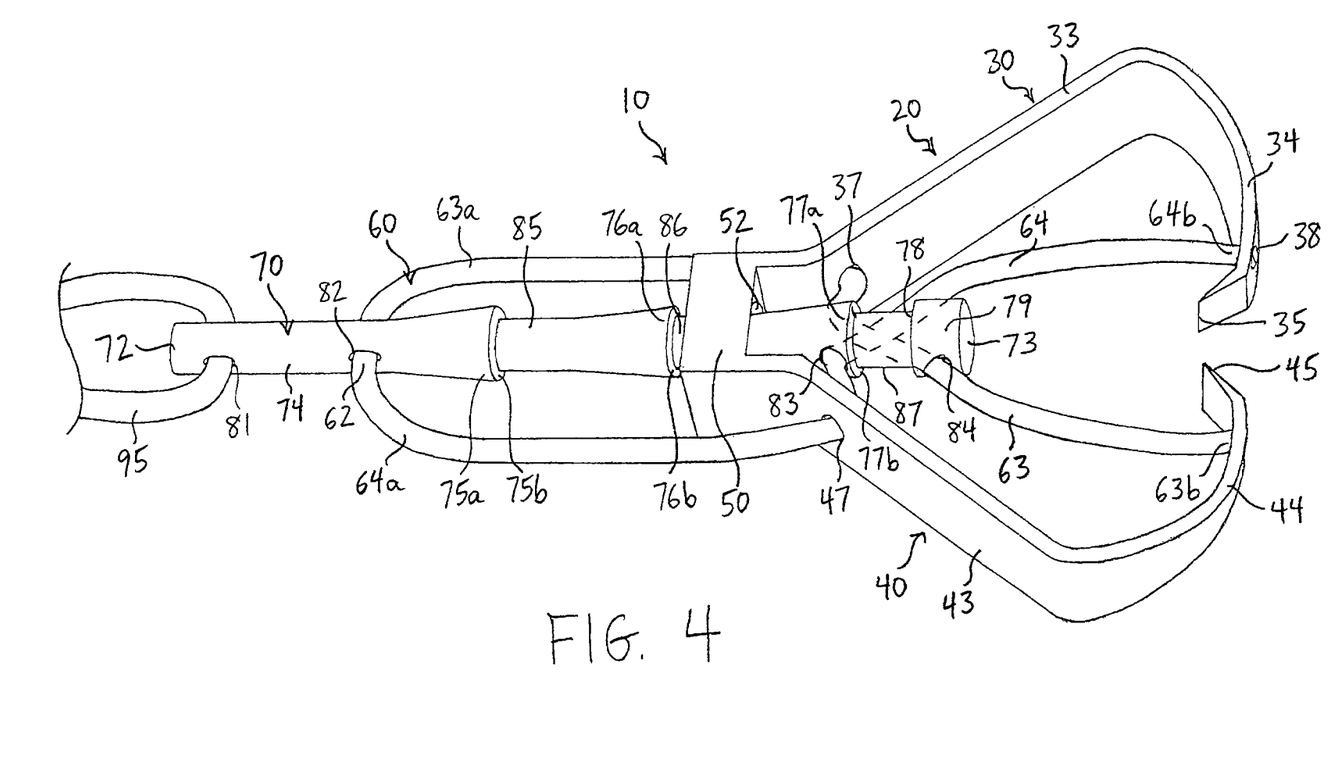
FIG. 4 is a perspective view showing components of the clip system of FIGS. 1-3 with the clip in a closed state.

At least a portion of the distal regions 34 and 44 of the first and second arms 30 and 40 are preferably sharpened to form tips 35 and 45, respectively, as seen in FIGS. 1-2. The tips 35 and 45 are configured to grasp and/or pierce tissue, particularly when the clip 20 is in a closed position as shown in FIG. 4 below.

As shown in FIG. 1, when the clip 20 is in an open state, the proximal and distal regions 32 and 34 of the first arm 30, as well as the proximal and distal regions 42 and 44 of the second arm 40, are each generally parallel to one another and oriented along a longitudinal axis L of the clip system 10. The tapered central region 33 extends at an angle $\alpha_1$, relative to the longitudinal axis L, between the proximal and distal regions 32 and 34 of the first arm 30, as shown in FIG. 1. Similarly, the tapered central region 43 extends at an angle $\alpha_2$, relative to the longitudinal axis L, between the proximal and distal regions 42 and 44 of the second arm 40. In this manner, the distal regions 34 and 44 of the first and second arms 30 and 40, respectively, are spaced apart from one another a predetermined distance when the clip is in the open state shown in FIGS. 1-2, thereby allowing tissue to be positioned between the distal regions 34 and 44 of the first and second arms 30 and 40.

The first and second arms 30 and 40 are biased to assume the open state when the distal regions 34 and 44 are no longer constrained by the catheter 90. The distal regions 34 and 44 may be biased to assume the open state either due to the inherent resilient properties of the material forming the first and second arms 30 and 40, or alternatively, the first and second arms 30 and 40 may be heat-set to assume the deployed configuration shown. The first and second arms 30 and 40 may be made from any suitable resilient material such as stainless steel, nitinol, plastic, and the like.

It will be appreciated that the clip 20 may have other configurations in the open state, besides the shape depicted in FIGS. 1-2. For example, one or more of the proximal regions 32 and 42, and/or the distal regions 34 and 44, may not be parallel to the longitudinal axis L. Further, the first and second arms 30 and 40 may comprise generally continuous outward curvatures between the proximal region 32 and the distal region 34. In still further alternatives, the tips 35 and 45 may be bent in radially inward directions when the clip is in the open state. Moreover, while the first and second arms 30 and 40 are shown as having a generally rectangular cross-sectional shape, the first and second arms 30 and 40 alternatively may have a cross-sectional shape that is round, square, triangular, pie-shaped, truncated cone, and the like.

The locking pin 70 interacts with the tether 60 and the clip 20 to facilitate incremental movement of the clip 20 between open and closed states, as explained in further detail below. The locking pin 70 has proximal and distal ends 72 and 73, respectively, and a main body 74 extending therebetween, generally along the longitudinal axis L of the clip system 10. At least a portion of the locking pin 70 is dimensioned to be disposed through a bore 52 formed in the base region 50 of the clip 20, as shown in FIG. 1. In this embodiment, the locking pin is dimensioned to be incrementally retracted in a proximal direction through the bore 52 in the clip 20 to facilitate incremental closure of the clip 20.

The locking pin 70 comprises at least one flared region, and preferably a plurality of flared regions, that facilitate incremental retraction in a proximal direction through the bore 52 of the clip 20. In the embodiment depicted, the locking pin 70 comprises a plurality of flared regions 75a, 76a and 77a, as shown in FIG. 1 and FIG. 3.

Figure 3:
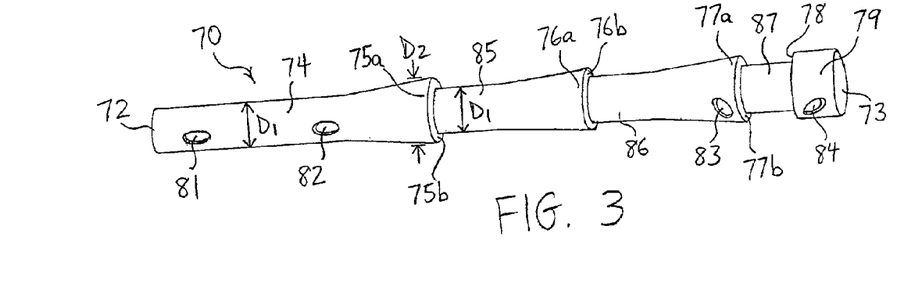
FIG. 3 is a perspective view showing a locking pin of FIG. 1 in isolation.

In this particular embodiment, the proximal end 72 of the locking pin 70 extends distally at a first diameter $D_1$, and then transitions in a tapered manner into a first flared region 75a having a second diameter $D_2$, which is greater than the first diameter $D_1$, as shown in FIG. 3. A first stepped region 75b is disposed between the first flared region 75a and a recessed region 85, such that the first stepped region 75b reduces the outer diameter from the second diameter $D_2$ of the first flared region 75a to a reduced diameter of the recessed region 85. In the embodiment shown, the reduced diameter of the recessed region 85 is the same as the first diameter $D_1$.

Similarly, the locking pin 70 further comprises a second flared region 76a having the second diameter $D_2$, and a second stepped region 76b is disposed between the second flared region 76a and a recessed region 86, as shown in FIG. 3. The second stepped region 76b reduces the outer diameter from the second diameter $D_2$ of the second flared region 76a to a reduced diameter, e.g., diameter $D_1$, of the recessed region 86. Further, a third flared region 77a comprises the second diameter $D_2$, and a third stepped region 77b is disposed between the third flared region 77a and a recessed region 87. The third stepped region 77b reduces the outer diameter from the second diameter $D_2$ of the third flared region 77a to a reduced diameter, e.g., diameter $D_1$, of the recessed region 87. Finally, a stop member 79 is positioned near the distal end 73 of the locking pin 70. The stop member 79 may comprise a diameter that is greater than or equal to the second diameter $D_2$. Preferably, in lieu of an angled taper from the recessed region 87 to the stop member 79, a step 78 is provided to limit maximum proximal retraction of the locking pin 70 through the bore 52 in the clip 20, as explained further below.

In one embodiment, the bore 52 in the base region 50 of the clip 20 comprises a tapered cylindrical shape. The bore 52 comprises a proximal end 53 having a third diameter, a distal end 55 having a fourth diameter, and a tapered region 54 disposed between the proximal and distal ends 53 and 55, as shown in FIG. 2. In one example, the second diameter $D_2$ of the locking pin 70 is less than the fourth diameter at the distal end 55 of the bore 52, but the second diameter $D_2$ is greater than the third diameter at the proximal end 53 of the bore 52, such that a sufficient proximal retraction force is required to pull the three flared regions 75a, 76a and 77a of the locking pin 70 incrementally through the bore 52. In an alternative embodiment, the bore 52 may comprises a substantially uniform, non-tapered inner diameter that is greater than the diameter $D_1$ but less than or about equal to the diameter $D_2$ of the locking pin 70, thereby requiring a similarly sufficient proximal retraction force to be imposed to pull the locking pin 70 through the bore 52 of the base region 50. The locking pin 70 may be formed from stainless steel, nitinol, plastic or the like. The bore 52 and/or the locking pin 70 may be configured to resiliently deform to allow passage of the three flared regions 75a, 76a and 77a incrementally through the bore 52 when a sufficient retraction force is applied.

The tether 60 is coupled to both the clip 20 and the locking pin 70 in a manner that facilitates incremental closure of the clip 20. In the embodiment shown, the tether 60 comprises one continuous loop of tether material, however, it will be appreciated that multiple tethers may be provided and coupled together in a manner to perform the intended functions described herein. Moreover, the tether 60 may be formed from one or more suitable materials, including but not limited to string, stainless steel wire, a chain material, or the like. In one example, the tether 60 is formed of a material that is not likely to be inadvertently severed by the sharpened tips 35 and 45 of the clip 20 if they come in contact during use.

The tether 60 is provided in a manner such that a proximal region 62 is disposed through a bore 82 formed in the locking pin 70, as shown in FIG. 1. The proximal region 62 is generally a midway point that separates first and second tether segments 63 and 64 of the tether 60. The first tether segment 63 has proximal and distal regions 63a and 63b, while the second tether segment 64 has proximal and distal regions 64a and 64b, as shown in FIG. 1.

The proximal region 63a of the first tether segment 63 may be disposed through a bore 37 formed in the clip 20 to facilitate guidance of the tether 60. The bore 37 may be disposed through the tapered central region 33 of the first arm 30, as depicted in FIG. 1. Alternatively, the bore 37 may be positioned further proximal or distal to the location depicted in FIG. 1, or the bore 37 may be omitted altogether such that the first tether segment 63 is positioned over or under the first arm 30, so long as the tether 60 can perform the functions described below. If the bore 37 is employed, then after passing through the bore 37, the first tether segment 63 extends distally as well as laterally in a direction from the first arm 30 towards the second arm 40. The distal region 63b of the first tether segment 63 is coupled to a second securing member 48 disposed on the distal region 44 of the second arm 40, as depicted in FIG. 1. The second securing member 48 secures the first tether segment 63 to the distal region 44 of the second arm 40.

The second tether segment 64 follows a similar yet symmetrically opposing pathway relative to the first tether segment 63, as shown in FIG. 1. In particular, the second tether segment 64 may be disposed through a bore 47 formed in the tapered central region 43 of the second arm 40 to facilitate guidance of the second tether segment 64. As with the bore 37 described above, the bore 47 may be positioned near a proximal end of the tapered central region 43, as depicted in FIG. 1, or may be positioned further proximal or distal to the location depicted, or the bore 47 may be omitted altogether such that the second tether segment 64 is positioned over or under the second arm 40, so long as the tether 60 can perform the functions described below. If the bore 47 is employed, then after passing through the bore 47, the second tether segment 63 extends distally as well as laterally in a direction from the second arm 40 towards the first arm 30. The distal region 64b of the second tether segment 64 is coupled to a first securing member 38, as best seen in FIG. 2 and FIG. 4, disposed on the distal region 34 of the first arm 30. The first securing member 38 secures the second tether segment 64 to the distal region 34 of the first arm 30.

Notably, the first and second tether segments 63 and 64 cross paths, but do not physically intersect, at a juncture 68 as shown in FIG. 1. The tether 60 therefore forms a loop shape between the proximal end 62 and the juncture 68. Distal to the juncture 68, the first and second tether segments 63 and 64 diverge from one another, as shown, such that the distal region 64b of the second tether segment 64 is coupled to the first securing member 38 of the first arm 30, and the distal region 63b of the first tether segment 63 is coupled to the second securing member 48 of the second arm 40.

In the embodiment of FIGS. 1-2 and FIG. 4, the first and second securing members 38 and 48 each comprise a bore formed in the distal regions 34 and 44 of the first and second arms 30 and 40, respectively. The bores of the first and second securing members 38 and 48 may be sized to frictionally engage the second and first tether segments 64 and 63, respectively. Alternatively, or in addition to a friction fit, distal ends of the first and second tether segments 63 and 64 may be adhered, welded, knotted, or otherwise secured within the bores of the second and first securing members 48 and 38, respectively. In further alternative embodiments, the first and second securing members 38 and 48 may not comprise the bores depicted, but rather may comprise hooks capable of securely engaging the first and second tether segments 63 and 64, or they may comprise other mechanical attachment features.

Figure 5:
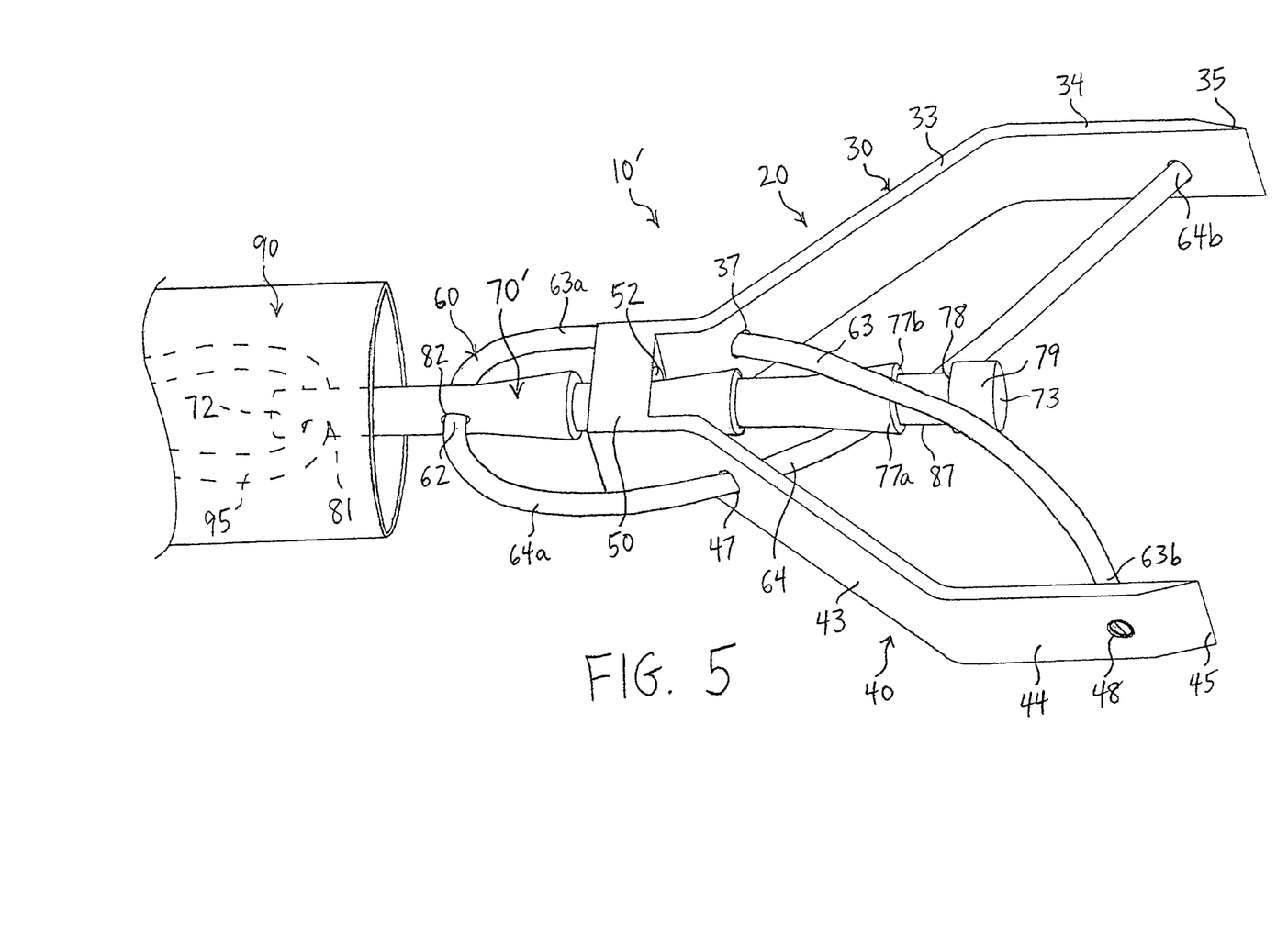
FIGS. 5-6 are, respectively, perspective views showing components of an alternative clip system with a clip in open and closed states, respectively.
Figure 6:
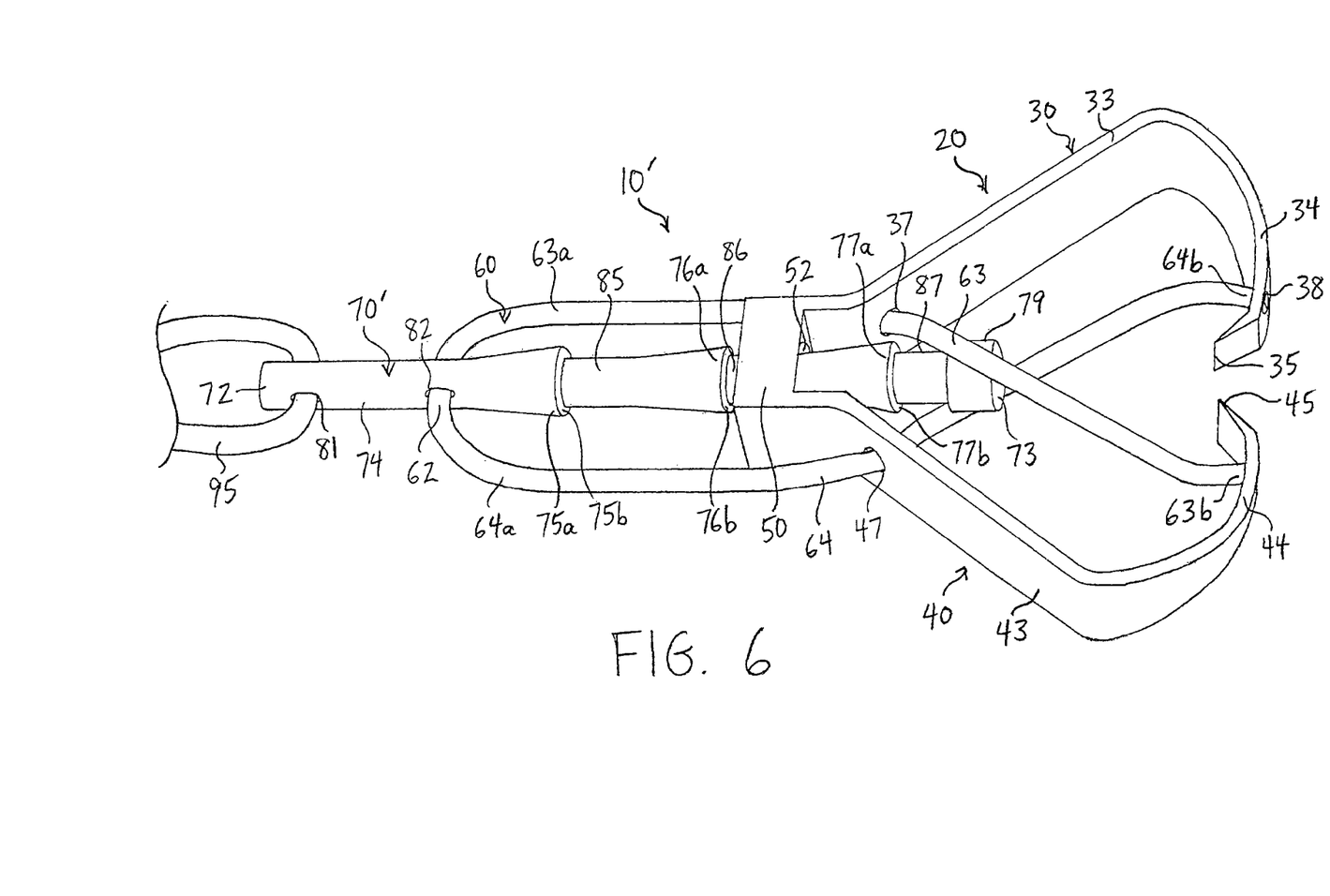

In the embodiment of FIG. 1, the first tether segment 63 is shown extending through an angled bore 84 formed in the locking pin 70, while the second tether segment 64 is shown extending through an angled bore 83 formed in the locking pin 70. The angled bores 83 and 84 are depicted as crossing paths at the junction 68. The angled bore 83 may be disposed within the locking pin 70 at a location above the angled bore 84 to accommodate passage of both tether segments 63 and 64. Alternatively, one of the angled bores 83 or 84 may be disposed entirely through the locking pin 70 at a location proximal to the other angled bore, such that the angled bores 83 and 84 do not longitudinally overlap. Still further, only one angled bore 83 or 84 may be disposed within the locking pin 70, to thereby accommodate only the second or first tether segment 64 or 63, respectively, and the tether segment that is not disposed through the locking pin 70 is disposed over or under the locking pin 70. In yet a further alternative, both the angled bores 83 and 84 may be omitted and the first and second tether segments 63 and 64 may each pass over the locking pin 70, under the locking pin 70, or one tether segment may pass over the locking pin 70 while the other tether segment passes under, as shown in FIGS. 5-6 below.

During use, the clip 20 has a delivery state, an open state, and a closed state. The clip system 10 is provided with the clip 20 in the delivery state, in which the clip 20 is disposed within a lumen 93 of the catheter 90. The lumen 93 of the catheter 90 is dimensioned such that the distal ends 34 and 44 of the first and second arms 30 and 40, respectively, are held adjacent to one another in the delivery state. Further, the locking pin 70 and the tether 60 are disposed within the lumen 93 of the catheter 90 and are coupled to the clip 20 as shown in FIG. 1. Preferably, when the clip 20 is in the delivery state, the locking pin 70 is positioned such that the first stepped region 75b is disposed immediately proximal to the base region 50 of the clip 20, with the recessed region 85 of the locking pin 70 disposed within the bore 52 of the base region 50, as depicted in FIG. 1.

Further, a retainer 95 is coupled to the locking pin 70 and configured for longitudinal manipulation of the locking pin 70. In the example of FIG. 1, the retainer 95 comprises a suture that is looped through a bore 81 formed near the proximal end 72 of the locking pin 70, such that the ends of the suture extend proximally within the catheter 90 for manipulation by a physician. However, various other retainer arrangements are possible. By way of example, alternative retainer arrangements to couple a suture, tether, cable, operating wire or other device to the locking pin 70, and to thereby longitudinally manipulate the locking pin 70, are described in U.S. Pat. Pub. No. 2007/0282355, the disclosure of which is hereby incorporated by reference in its entirety.

The clip system 10 may be delivered to a target tissue site endoscopically or using another suitable approach. If an endoscopic technique is employed, the catheter 90 with the clip system 10 loaded therein is directed towards the target tissue site in the delivery state. When a desirable location is determined, e.g., using endoscopic visualization, the catheter 90 may be translated proximally relative to the clip 20 to move the clip between the delivery state and the open state.

In the open state, shown in FIGS. 1 and 2, the distal ends 34 and 44 of the first and second arms 30 and 40, respectively, tend to be spaced apart from one another. The first and second arms 30 and 40 are biased to assume the open state when the distal ends 34 and 44 are no longer constrained by the catheter 90. As noted above, the distal ends 34 and 44 may be biased to assume the open state either due to the inherent resilient properties of the material forming the first and second arms 30 and 40, or alternatively, the first and second arms 30 and 40 may be heat-set to assume the deployed configuration shown. Notably, the catheter 90 is shown proximal to the clip 20 in FIG. 1 for illustrative purposes only, however, when the clip 20 is in the open state the distal end 92 of the catheter 90 may be positioned to abut the tapered central regions 33 and 43 of the clip 20 in the vicinity of the bores 37 and 47. Further, when the clip 20 is in the open state, the clip 20 may be positioned such that target tissue is disposed between the first and second arms 30 and 40 of the clip 20. Such positioning may be achieved under endoscopic visualization by an endoscope, or using one or more other visualization techniques.

Upon desired positioning of the clip 20 relative to the target tissue in the open state, the locking pin 70 then is incrementally retracted in a proximal direction through the bore 52 in the clip 20 to facilitate incremental closure of the clip 20. For example, a physician may hold the catheter 90 steady against the tapered central regions 33 and 43 of the clip 20, while proximally retracting both free ends of the retainer 95 that is coupled to the locking pin 70. At this time, a retraction force is imposed that is sufficient to pull the second flared region 76a having the second diameter $D_2$ through the bore 52 of the base region 50 of the clip 20. As the locking pin 70 is retracted relative to the clip 20, the first and second tether segments 63 and 64 are also retracted proximally and pull upon the distal regions 44 and 34 of the second and first arms 40 and 30, respectively, thereby causing the distal regions 44 and 34 to bow radially inward as shown in FIG. 4. In this closed state, the tips 35 and 45 of the first and second arms 30 and 40, respectively, and/or other portions of the distal regions 34 and 44, are configured to grasp tissue and facilitate tissue closure and hemostasis.

At this time, the second stepped region 76b is disposed proximal to the bore 52 of the base region 50, thereby forming a step that limits subsequent distal advancement of the locking pin 70 to ensure a secure closure. Optionally, the locking pin 70 may be further incrementally advanced proximally through the bore 52 of the base region 50, and in particular, the third flared region 77a having the second diameter $D_2$ may be pulled through the bore 52 of the base region 50 of the clip 20 such that the third stepped region 77b is disposed proximal to the bore 52 of the base region 50. Ultimately, the step 78 of the stop member 79 limits maximum proximal retraction of the locking pin 70 through the bore 52 in the clip 20.

In accordance with one aspect, a physician may incrementally move the clip 20 between open and closed states using the locking pin 70 and the first and second tether segments 63 and 63. While three flared regions 75a, 76a and 77a and corresponding stepped regions 75b, 76b and 77b are depicted on the locking pin 70, it will be appreciated that additional flared and stepped regions may be provided, thereby increasing the incremental closure abilities of the clip 20.

When the clip 20 is in the desired closed state, the retainer 95 may be disengaged from the clip 20 by proximally retracting one free end of the retainer 95 such that the other free end is pulled through the bore 81 of the locking pin 70. However, as noted above, various alternative retainer arrangements that may be used to couple a retainer to, and disengage from, the locking pin 70 are described in U.S. Pat. Pub. No. 2007/0282355, the disclosure of which is hereby incorporated by reference in its entirety.

Referring now to FIGS. 5-6, components of an alternative clip system 10' are generally identical to corresponding components of the clip system 10 of FIGS. 1-4, except as noted below. In FIGS. 5-6, an alternative locking pin 70' is provided that omits the angled bores 83 and 84. In this embodiment, the first tether segment 63 passes over the locking pin 70' while the second tether segment 64 passes under the locking pin 70'. Advantageously, in this example, full proximal retraction of the locking pin 70' up to the step 78 of the stop member 79 may be facilitated without impedance from the first and second suture segments 63 and 64 passing directly though the locking pin.

In a further alternative, the first and second tether segments 63 and 64 may not cross paths with one another, i.e., the first tether segment 63 may be coupled to the distal region 34 of the first arm 30, and the second tether segment 64 may be coupled to the distal region 44 of the second arm 40, such that the first and second tether segments 63 and 64 are generally parallel to one another along their respective lengths and along the longitudinal axis L.

Figure 7:
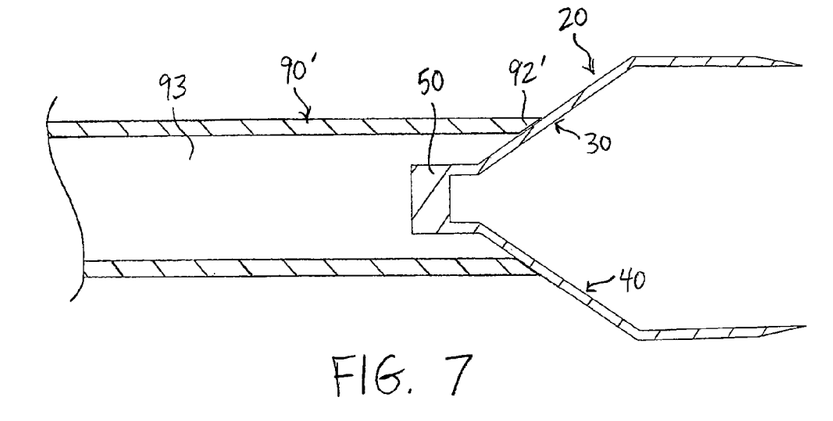
FIG. 7 is a side-sectional view of an alternative delivery catheter engaging the clip of FIG. 1.
Figure 8:
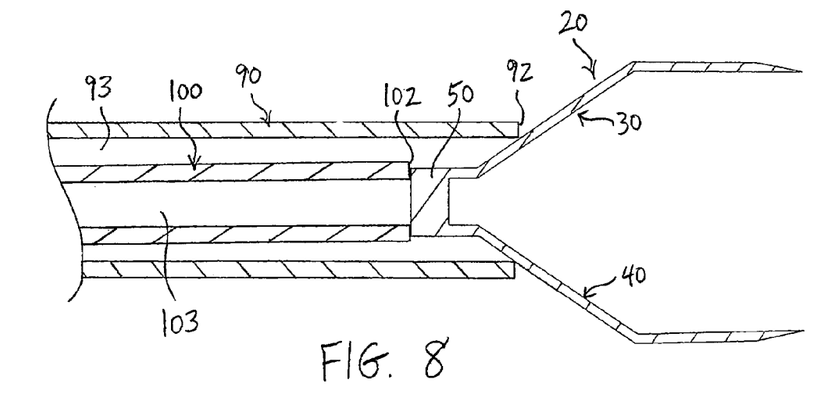
FIG. 8 is a side-sectional view of an inner catheter engaging the clip of FIG. 1.

Referring now to FIGS. 7-8, further alternative embodiments depicting engagement of delivery components with the clip 20 are shown. In FIGS. 7-8, it should be noted that the tether 60 and the locking pin 70 are omitted for illustrative purposes only. In FIG. 7, an alternative delivery catheter 90' comprises a distal end 92' that is tapered to engage the first and second arms 30 and 40 of the clip 20 in a flush manner. In use, the locking pin 70 is translated proximally relative to the delivery catheter 90' to close the arms of the clip 20 via the tether 60, as described above.

In FIG. 8, a delivery system further comprises an inner catheter 100 having a distal end 102 and a lumen 103, where the inner catheter 100 is dimensioned for longitudinal movement within the lumen 93 of the outer catheter 90. During delivery, the clip 20 is disposed within the lumen 93 of the outer catheter 90 at a location distal to the inner catheter 100. The first and second arms 30 and 40 of the clip 20 then are opened distal to the outer catheter 90, as shown in FIG. 8. The inner catheter 100 then is advanced distally to abut the base region 50 of the clip 20. At this time, a proximal portion of the locking pin 70 and the entirety of the retainer 95 are disposed within the lumen 103 of the inner catheter 100. The outer catheter 90 and the inner catheter 100 then may be held steady while the locking pin 70 is retracted proximally to close the first and second arms 30 and 40 of the clip 20.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A system for deploying at least one clip during a medical procedure, the system comprising:
    a clip having first and second arms, wherein distal regions of the first and second arms tend to be spaced apart from each other when the clip is in an open state, and wherein the distal regions of the first and second arms are adjacent to each other when the clip is in a closed state;
    a locking pin having a proximal end, a distal end, and a main body extending therebetween, wherein the locking pin is coupled to the clip and disposed for incremental movement relative to the clip; and
    a tether coupled to the locking pin, wherein a first tether segment is secured to the distal region of the second arm, and a second tether segment is secured to the distal region of the first arm, wherein the first and second tether segments cross over each other,
    wherein proximal retraction of the locking pin causes a proximal refraction of the first and second tether segments to move the clip between the open and closed states.

2. The system of claim 1 wherein the tether is coupled to the locking pin through a bore formed in the locking pin.

3. The system of claim 1 further comprising a retainer releasably coupled to the locking pin, wherein proximal retraction of the retainer causes proximal retraction of the locking pin.

4. The system of claim 3 wherein the retainer comprises a suture that is looped through a bore formed in the locking pin.

5. The system of claim 1 further comprising:
    a first securing member disposed on the distal region of the first arm for securing the second tether segment to the distal region of the first arm; and
    a second securing member disposed on the distal region of the second arm for securing the first tether segment to the distal region of the second arm.

6. The system of claim 5 wherein the first and second securing members comprise bores formed in the distal regions of the first and second arms, respectively.

7. The system of claim 1 wherein the clip further comprises a base region having a bore formed longitudinally therethrough, wherein at least a portion of the locking pin is disposed through the bore in the base region.

8. The system of claim 7 wherein the locking pin comprises at least one region having a first diameter, and further comprises at least one flared region having a second diameter, wherein the second diameter is greater than the first diameter,
    wherein the second diameter of the flared region is greater than a diameter of the bore of the base region such a sufficient retraction force must be imposed upon the locking pin to incrementally proximally retract the locking pin through the base region of the clip.

9. The system of claim 1 wherein the first tether segment is disposed around an external surface of the locking pin at a location proximal to attachment of the first tether segment to the distal region of the second arm.

10. The system of claim 1 wherein the first tether segment is guided through a bore formed in the first arm at a location proximal to attachment of the first tether segment to the distal region of the second arm, and the second tether segment is guided through a bore formed in the second arm at a location proximal to attachment of the second tether segment to the distal region of the first arm.

11. A system for deploying at least one clip during a medical procedure, the system comprising:
    a clip having first and second arms, wherein distal regions of the first and second arms tend to be spaced apart from each other when the clip is in an open state, and wherein the distal regions of the first and second arms are adjacent to each other when the clip is in a closed state;
    a locking pin having a proximal end, a distal end, and a main body extending therebetween, wherein the locking pin is coupled to the clip and disposed for incremental movement relative to the clip;
    a tether coupled to the locking pin, wherein a first tether segment is secured to the distal region of the second arm, and a second tether segment is secured to the distal region of the first arm,
    wherein proximal retraction of the locking pin causes a proximal refraction of the first and second tether segments to move the clip between the open and closed states; and
    a retainer releasably coupled to the locking pin, wherein proximal retraction of the retainer causes proximal retraction of the locking pin,
    wherein the retainer comprises a suture that is looped through a bore formed in the locking pin.

12. A system for deploying at least one clip during a medical procedure, the system comprising:
    a clip having first and second arms, wherein distal regions of the first and second arms tend to be spaced apart from each other when the clip is in an open state, and wherein the distal regions of the first and second arms are adjacent to each other when the clip is in a closed state;
    a locking pin having a proximal end, a distal end, and a main body extending therebetween, wherein the locking pin is coupled to the clip and disposed for incremental movement relative to the clip; and
    a tether coupled to the locking pin, wherein a first tether segment is secured to the distal region of the second arm, and a second tether segment is secured to the distal region of the first arm,
    wherein proximal retraction of the locking pin causes a proximal refraction of the first and second tether segments to move the clip between the open and closed states, and
    wherein the first tether segment is guided through a bore formed in the first arm at a location proximal to attachment of the first tether segment to the distal region of the second arm, and the second tether segment is guided through a bore formed in the second arm at a location proximal to attachment of the second tether segment to the distal region of the first arm.

\* \* \* \* \*

UNITED STATES PATENT AND TRADEMARK OFFICE
CERTIFICATE OF CORRECTION

PATENT NO. : 8,764,774 B2  
APPLICATION NO. : 13/290580  
DATED : July 1, 2014  
INVENTOR(S) : Sigmon, Jr.

Page 1 of 1

It is certified that error appears in the above-identified patent and that said Letters Patent is hereby corrected as shown below:

In the Claims

Column 9, claim 1, line 23, before "of the first and second" replace "refraction" with --retraction--.

Column 10, claim 11, about line 25, before "of the first and second" replace "refraction" with --retraction--.

Column 10, claim 12, about line 49, before "of the first and second" replace "refraction" with --retraction--.

Signed and Sealed this
Fourth Day of November, 2014

Michelle K. Lee
*Deputy Director of the United States Patent and Trademark Office*